United States Patent [19]

Ramanathan

[11] 3,932,122
[45] Jan. 13, 1976

[54] AZO COMPOUNDS, THEIR MANUFACTURE AND USE
[75] Inventor: Visvanathan Ramanathan, Basel, Switzerland
[73] Assignee: Ciba-Geigy AG, Basel, Switzerland
[22] Filed: June 12, 1973
[21] Appl. No.: 369,359

Related U.S. Application Data
[62] Division of Ser. No. 190,678, Oct. 19, 1971, abandoned.

[30] Foreign Application Priority Data
Oct. 23, 1970 Switzerland.................. 15658/70
Sept. 30, 1971 Switzerland.................. 14211/71

[52] U.S. Cl. ............... 8/41 C; 8/41 R; 260/156
[51] Int. Cl.² ............... C09B 29/36; D06P 3/56
[58] Field of Search ............... 260/156, 153–155; 8/41 R, 41 C

[56] References Cited
UNITED STATES PATENTS
3,640,674   2/1972   Berrie et al. .................. 8/41 C FOREIGN PATENTS OR APPLICATIONS
727,066   7/1969   Belgium .................. 260/156

1,964,690   7/1970   Germany .................. 260/156
1,061,948   3/1967   United Kingdom .................. 260/156
1,250,071   10/1971   United Kingdom .................. 260/156

Primary Examiner—Leland A. Sebastian
Assistant Examiner—David Leland
Attorney, Agent, or Firm—Joseph G. Kolodny; Edward McC. Roberts; Prabodh I. Almaula

[57] ABSTRACT

Azo compounds of the formula

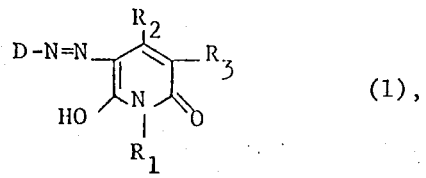

wherein D represents the radical of a diazo component, $R_1$ and $R_3$ each represent a hydrogen atom or a substituent and $R_2$ represents a substituent, and which contain at least one carboxy group that may not, however, be bonded in the adjacent position to the azo bridge directly to the ring.

6 Claims, No Drawings

AZO COMPOUNDS, THEIR MANUFACTURE AND USE

This is a Divisional of application Ser. No. 190,678, filed on October 19, 1971, now abandoned.

The present invention relates to new azo compounds of the formula

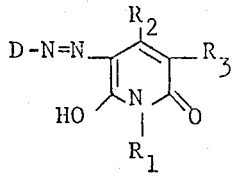

wherein B represents the radical of a diazo component, $R_1$ and $R_3$ each represent a hydrogen atom or a substituent and $R_2$ represents a substituent, and which contain at least one carboxy group that may not, however, be bonded in the adjacent position to the azo bridge directly to the ring.

D is preferably the radical of a diazo component of the benzene or naphthalene series.

The carboxy group can be contained both in the radical D of the diazo component and in the substituents $R_1$ and $R_2$. It can also be in the form of a salt, for example of a potassium, sodium or ammonium salt.

The carboxy group that is not in the adjacent position to the azo bridge is preferably bonded in the form —X—COOH, wherein X represents a direct bond or a divalent radical, in particular a radical of the formula —$CH_2$, —$CH_2$—$CH_2$—, —$OCH_2$, —$SCH_2$—, —NH-$COCH_2$—$CH_2$— or represents

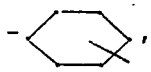

wherein X represents a divalent radical if the group —X—COOH is bonded to D in the adjacent position to the azo bridge, or if $R_2$ is a group —X—COOH.

As substituents $R_1$, $R_2$ and $R_3$ there may be considered especially: $R_1$ is a hydrogen atom, an alkyl radical, by which a cycloalkyl radical is also to be understood, an aryl or aralkyl radical, a heterocyclic radical or an amino group, which radicals may also be substituted; $R_2$ is an alkyl, aryl or aralkyl radical, which radicals may also be substituted, also a heterocyclic radical, an ester or carbonamide group; $R_3$ is a hydrogen or halogen atom, in particular a chlorine atom, a cyano, sulphonyl, ester, acyl, carbonamide or sulphonamide group.

If the carboxy group is in the substituent $R_1$, this latter preferably has the form
  -alkyl-X-COOH, -alkyl-aryl-X-COOH,
  -aryl-X-COOH, heterocycle-X-COOH,
  -NR-alkyl-aryl-X-COOH,
  -NR-aryl-alkyl-X-COOH,
  -NR-CO-alkyl-X-COOH or
  -NR-CO-aryl-X-COOH,
where R represents a hydrogen atom or a low molecular alkyl or aryl radical and X has the meaning indicated above.

The radical D of the diazo component can also contain a further azo group besides the usual substituents in the case of azo compounds, especially groups which not impart solubility in water such, for example, as halogen atoms, nitro, alkyl, alkoxy, acylamino, carbalkoxy, alkylsulphone, acyloxy or trifluoromethyl groups.

In particular, D can contain a second hydroxypyridone radical bonded via an azo bridge and which has the structure illustrated in the formula (1). Also possible are therefore azo compounds of the formula

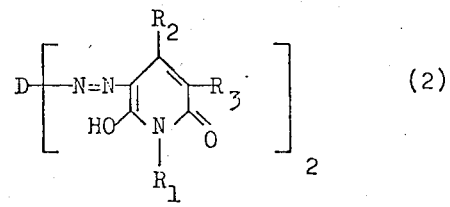

The invention relates furthermore to azo compounds of the formula

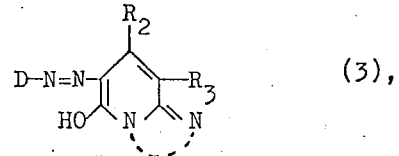

in which between the two nitrogen atoms of the pyridone radical there is located a carbon bridge to form a second ring, and wherein the symbols D, $R_2$ and $R_3$ have the meanings indicated above.

The new azo compounds are obtained by coupling diazo compounds of amines of the formula D-$NH_2$ with hydroxypyridone compounds of the formula

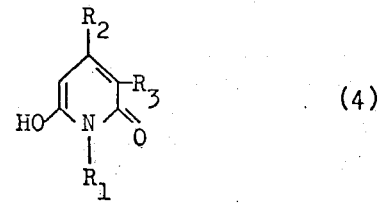

or of the formula

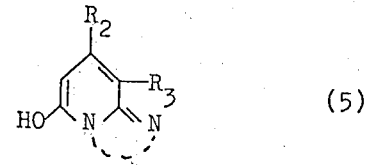

to the above cited compounds of the formulae (1) or (3), the starting materials being so chosen that the molecule of the azo compound contains a carboxy group that is not bonded in the adjacent position to the azo bridge directly to the ring.

As examples of amines whose diazo compounds are suitable for the manufacture of compounds of the formulae (1) or (3) there may be mentioned:
  3-aminobenzoic acid,
  3-aminophenoxyacetic acid,
  4-aminoazobenzene-4'-carboxylic acid,
  3-nitroaniline,
  3,3'-diaminodiphenylmethane,
  3,5-diaminobenzoic acid.

As examples of coupling components of the formulae (4) or (5) there may be mentioned:
  3-cyano-6-hydroxy-4-methyl-2-pyridone,
  1-β-hydroxyethyl-3-cyano-6-hydroxy-4-methyl-2-pyridone,
  3-cyano-6-hydroxy-4-carboxy-methyl-2-pyridone,
  3-cyano-6-hydroxy-4-carboxy-methyl-1-ethyl-2-pyridone, the compounds of the formulae

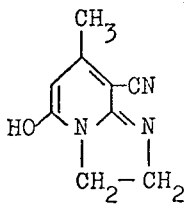

and

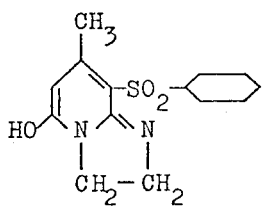

The diazotisation of the cited diazo components can be carried out, for example, with the assistance of aqueous mineral acid and sodium nitrite or with a solution of nitrosylsulphuric acid in concentrated sulfuric acid.

The coupling can likewise be carried out in a manner which is in itself known, for example in a neutral to acid medium, optionally in the presence of sodium acetate or similar buffer substances which influence the rate of coupling, such as, for example, dimethylformamide, pyridine or its salts.

The azo compounds according to the invention are valuable dyestuffs.

The new dyestuffs, their mixtures with one another and their mixtures with other azo dyestuffs are outstandingly suitable for dyeing and printing leather, wool, silk and above all synthetic fibres, such as, for example, acrylic or acrylonitrile fibres, of polyacrylonitrile or of copolymers of acrylonitrile and other vinyl compounds, such as acrylic esters, acrylamides, vinylpyridine, vinyl chloride or vinylidene chloride, or of copolymers of dicyanoethylene and vinyl acetate, as well as of acrylonitrile block copolymers, fibres of polyurethanes, polypropylene fibres and also cellulose triacetate and cellulose 2½-acetate and especially fibres of polyamides, such as nylon-6, nylon-6,6 or nylon-12, or of aromatic polyesters, such as those of terephthalic acid and ethylene glycol or 1,4-dimethylcyclohexane, and copolymers of terephthalic and isophthalic acid and ethylene glycol.

For dyeing in aqueous liquors, the water-insoluble dyestuffs are appropriately used in a finely divided form and dyeing is carried out with the addition of dispersing agents, such as sulphite cllulose waste lye or synthetic detergents, or a combination of different wetting agents and dispersing agents. As a rule it is advisable to convert the dyestuffs to be used, before dyeing, into a dyeing preparation which contains a dispersing agent and finely divided dyestuff in such a form that on dilution of the dyestuff preparations with water a fine dispersion results. Such dyestuff preparations can be obtained in a known manner, for example by grinding the dyestuff in the dry or wet form, with or without the addition of dispersing agents in the grinding process.

To achieve strong dyeings on polyethylene terephthalate fibres it proves advisable to add a swelling agent to the dyebath, or to carry out the dyeing process under pressure at temperatures above 100°C, for example at 120°C. Suitable swelling agents are aromatic carboxylic acids, for example salicyclic acid, phenols, such as, for example, o- or p-hydroxydiphenyl, and aromatic halogen compounds, such as o-dichlorobenzene, or diphenyl.

For thermofixing the dyestuff, the padded polyester fabric is heated, appropriately after prior drying, for example in a warm stream of air, to temperatures of above 100°C, for example between 180° and 210°C.

The dyeings obtained in accordance with the present process can be subjected to an after-treatment, for example, by heating with an aqueous solution of a non-ionic detergent.

Instead of being applied by impregnation, the dyestuffs indicated can, according to the present process, also be applied by printing. For this purpose a printing ink, for example, is used, which contains the finely disperse dyestuff in addition to the auxiliaries which are customary in printing, such as setting agents and thickeners.

The present process yields strong dyeings and prints of good fastness properties.

The new water-insoluble dyestuffs can also be used for the spin dyeing of polyamides, polyesters and polyolefines. The polymer to be dyed is appropriately mixed, in the form of powders, granules or chips, as a ready-to-use spinning solution or in the fused state, with the dyestuff which is introduced in the dry state or in the form of a dispersion or solution in a solvent, which is volatile if desired. After homogeneous distribution of the dyestuff in the solution or melt of the polymer, the mixture is processed in a known manner by casting, pressing or extrusion to give fibres, yarns, monofilaments, films and the like.

The new dyestuffs are also suitable for the multicolour printing of textile materials which consist of hydrophobic, synthetic, organic fibres which are free of amino groups, because resist effects are achievable on textile materials of such fibres with the new dyestuffs. Here, the procedure is that the textile material is padded with the new dyestuffs containing carboxyl groups, the padded textile material is dried and printed with an alkaline printing paste which can contain optical brighteners which are free of carboxyl groups, white pigments which are free of carboxyl groups or other dyestuffs which are free of carboxyl groups, the fabric is heat-set, and the salt of the dyestuff containing carboxyl groups is subsequently eluted from the printed areas.

As synthetic fibres which can be dyed or printed in this manner there may be mentioned acrylic fibres, fibres of polyurethanes, fibres based on polyepoxy compounds or polyolefine fibres, such as polypropylene, especially nickel-modified or unmodified polypropylene, and above all fibres of aromatic polyesters, such as those from terephthalic acid and ethylene glycol or 1,4-dimethylolcyclohexane, and of copolymers of terephthalic acid and isophthalic acid and ethylene glycol, as well as cellulose triacetate and cellulose 2½-acetate. The fibres to be printed must not contain any free amino groups.

Further possibilities are mixed fabrics of the above-mentioned fibres and hydrophilic fibres, especially cellulose fibres and wool fibres. Polyester-cotton and polyester-wool mixtures may also be mentioned.

The textile materials will as a rule be woven fabrics, knitted fabrics or other sheet-like structures, such as fleeces (non-wovens).

The new dyestuffs containing carboxyl groups can be in the form of salts of volatile organic bases or in the form of ammonium salts.

The padding liquor will as a rule be aqueous. In addition to the dyestuff it can also contain, if required, further auxiliaries, such as sodium salts of highly concentrated naphthalenesulphonic acid-formaldehyde resins, sulphite cellulose waste lye products, condensation products of higher alcohols and ethylene oxide, polyglycol ethers of fatty acid amides and alkylphenols, sulphosuccinic acid esters or Turkey-red oil. The padding liquor can however also be a solution of the dyestuff.

After squeezing out to 20–200% by weight of the fibre weight, the textile material is dried. The drying can for example be effected with steam or preferably with a stream of warm air at between 70° and 150°C for 10 to 300 seconds.

Thereafter, the fabric is printed with an alkaline printing paste which contains a heat-resisitant alkaline compound, such as an alkali carbonate, such as sodium carbonate or potassium carbonate, or above all alkali hydroxides, such as sodium hydroxide or potassium hydroxide. The amount of the alkali has to be so chosen that the dyestuff present on the fibre is reliably converted into the alkali salt. If the resist remains white, the resist paste can contain white pigments, such as titanium dioxide or zinc oxide. The printing paste furthermore contains the customary additives, such as thickeners, for example gum arabic or methylcellulose.

In order to achieve two colour prints, dyestuffs which are resistant to alkali, in particular dispersion dyestuffs, such as are listed, for example, in the Colour Index, will further be added to the printing paste. These dyestuffs must not contain any carboxyl groups.

Furthermore, optical brighteners which possess an affinity for the organic fabric (such as nylon fabric and above all cellulose acetate and polyester fabric) can also be introduced into the alkaline printing paste. In addition to a dispersion dyestuff free of carboxyl groups, the printing paste can also contain dyestuffs of other tinctorial categories, such as, for example, water-soluble or water-insoluble dyestuffs possessing fibre-reactive groups, such as dichlorotriazinee or monochlorotriazine groups, chloroacetylamino groups and acrylamide groups. The use of water-soluble fibre-reactive dyestuffs is of interest particularly in those cases where mixed fabrics containing cellulose or containing wool, and especially mixed fabrics containing polyester fibres, are used as the substrate. If printing pastes with fibre-reactive dyestuffs are used, the alkali treatment can be adapted to the modern methods for fixing reactive dyestuffs (for example alkali-shock treatment).

Further possible dyestuffs for printing are also optical brighteners.

After printing, the textile material can be dried either with steam or with hot air or can, as it is, be subjected to fixing.

The fixing of the dyestuff or dyestuffs on the textile material is carried out hot at 100° to 260°C, preferably from 150° to 230°C, but at lower temperatures in the case of polymers of low softening point, preferably by means of dry heat (thermosol process), in suitable equipment for this purpose. Superheated steam can also be used. Prints on polypropylene are thermofixed at temperatures below 140°C.

After fixing, the printed material is washed. It can be washed either in organic or, preferably, in aqueous liquors. The usual surface-active agents or detergents are used for this purpose.

In the examples which follow the parts denote parts by weight unless otherwise stated and the percentages denote percentages by weight.

EXAMPLE 1

6.85 Parts of 3-aminobenzoic acid are made into a paste with 15 parts by volume of concentrated hydrochloric acid and the resulting paste is diluted with 100 parts of water. 12.5 Parts by volume of 4N sodium nitrite solution are added dropwise at 0°–5°C and stirring is continued for 30 minutes. The resulting diazo solution is filtered clear and added at 0°–5°C to a solution of 7.5 parts of 3-cyano-6-hydroxy-4-methyl-2-pyridone which has been dissolved brilliantly alkaline in 650 parts of water and sodium hydroxide. The reaction mixture is rendered neutral to Congo red with sodium acetate solution. Upon completion of the coupling the precipitated dyestuff is filtered, washed with water and dried, to yield the dyestuff of the formula

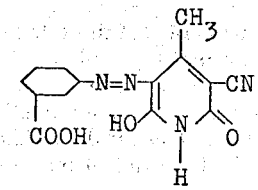

which dyes polyester and cellulose acetate fibres in yellow shades.

EXAMPLE 2

8.35 Parts of 3-aminophenoxyacetic acid are made into a paste with 15 parts by volume of concentrated hydrochloric acid and the resulting paste is diluted with 100 parts of water. 12.5 Parts by volume of 4N sodium nitrite solution are added dropwise at 0°–5°C and stirring is continued for 30 minutes. 9.7 Parts of 1-β-hydroxyethyl-3-cyano-6-hydroxy-4-methyl-2-pyridone are dissolved brilliantly alkaline in 650 parts of water to which sodium hydroxide is added. The reaction mixture is rendered neutral to Congo red with sodium acetate solution. Upon completion of the coupling the precipitated dyestuff is filtered, washed with water and dried, to yield the dyestuff of the formula

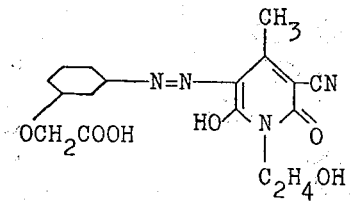

which dyes polyester fibres in yellow shades.

EXAMPLE 3

12.05 Parts of 4'-aminoazobenzene-4-carboxylic acid are made into a paste with 15 parts by volume of concentrated hydrochloric acid and the resulting paste is diluted with 1,500 parts of ice water. 12.5 Parts by volume of 4N sodium nitrite solution are added dropwise at 0°–5°C and stirring is continued for 2 hours.

7.5 Parts of 3-cyano-6-hydroxy-4-methyl-2-pyridone are dissolved brilliantly alkaline in 650 parts of water to which sodium hydroxide is added. The above resulting diazo solution is added at 0°–5°C to the pyridone solution. The reaction mixture is rendered neutral to Congo red with sodium acetate solution. Upon completion of the coupling the precipitated dyestuff is filtered, washed with water and dried, to yield the dyestuff of the formula

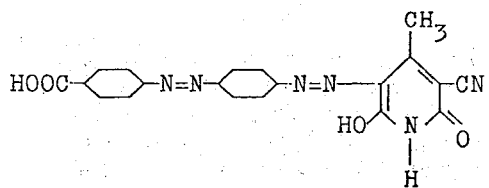

which dyes polyester fibres in orange shades.

EXAMPLE 4

6.9 Parts of 3-nitroaniline are made into a paste with 15 parts by volume of hydrochloric acid and the resulting paste is diluted with 200 parts of ice water. 12.5 Parts by volume of 4N sodium nitrite solution are added dropwise at 0°–5°C and stirring is continued for 1 hour. The diazo solution is filtered clear and added to a solution of 9.7 parts of 3-cyano-6-hydroxy-4-carboxymethyl-2-pyridone in 200 parts of alcohol. The coupling mixture is rendered neutral to Congo red with sodium acetate solution. Upon completion of the coupling the precipitated dyestuff is filtered, washed with water and dried. The dyestuff of the formula

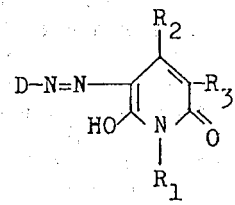

dyes polyester fibres in yellow shades having very good fastness properties.

The coupling component was obtained by saponification of 3-cyano-6-hydroxy-4-ethoxycarbonylmethyl-2-pyridone with 5% alcoholic sodium hydroxide solution.

According to the same process dyestuffs of the formula $$D-N=N-\underset{HO}{\overset{R_2}{\underset{|}{\bigcirc}}}\overset{R_3}{\underset{R_1}{N}}O$$

wherein the meaning of $D$, $R_1$, $R_2$ and $R_3$ is stated in the following table, are obtained which dye polyester fibres in the shades indicated in the last column.

| | D | $R_1$ | $R_2$ | $R_3$ | Shade |
|---|---|---|---|---|---|
| 1 | HOOC–⌬– | –CH₃ | –CH₃ | –CN | yellow |
| 2 | ⌬– (COOH) | –C₂H₅ | " | " | " |
| 3 | HOOC–H₂CH₂C–⌬– | –C₂H₄OCOCH₃ | " | " | " |
| 4 | ⌬–SCH₂COOH | –⌬ | " | " | " |
| 5 | ⌬– (COOH) | –C₂H₄OH | " | " | " |
| 6 | " | –C₃H₆OCH₃ | " | " | " |
| 7 | HOOC–⌬–⌬– | –C₃H₆OC₂H₅ | " | " | " |
| 8 | HOOCH₄C₂S–⌬– | –CH₂COOC₂H₅ | –CH₃ | –CN | yellow |
| 9 | HOOCH₄C₂OCHN–⌬– | –⌬(H) | –⌬ | " | " |
| 10 | HOOC–⌬⌬ | –CH(CH₃)₂ | CH₃ | SO₂CH₃ | orange |
| 11 | ⌬(CH₃)(COOH) | –C₂H₄–⌬ | " | –CN | yellow |
| 12 | HOOC–⌬(NO₂) | –C₂H₄–⌬N | " | " | " |
| 13 | HOOC–⌬(CF₃) | –C₂H₄Cl | –iso C₄H₉ | " | " |

-continued

| | D | R₁ | R₂ | R₃ | Shade |
|---|---|---|---|---|---|
| 14 | HOOC–⟨Br⟩–CH₃ | –C₂H₄O–⟨⟩ | CH₃ | " | " |
| 15 | ⟨OCH₂COOH, NO₂⟩ | –C₂H₄S–⟨⟩ | –CH₂CONHC₃H₆OC₂H₅ | " | reddish yellow |
| 16 | HO–⟨COOH⟩ | –CH₂–⟨tetrahydrofuran⟩ | –C₂H₄–⟨⟩ | CN | orange |
| 17 | ⟨Cl, COOH⟩ | –C₂H₄CN | CH₃ | " | yellow |
| 18 | HOOC–⟨phthalimide-N-phenyl⟩ | –C₂H₄OC₂H₄CN | " | " | " |
| 19 | H₃CO–⟨OCH₃, COOH⟩ | –C₃H₆OCOCH₂–⟨⟩ | " | –SO₂–⟨⟩ | orange |
| 20 | HOOCHC=HC–⟨⟩ | –C₂H₄OCOCH₂O–⟨⟩ | " | CN | yellow |
| 21 | HOOC–⟨CN⟩ | –C₂H₄OCO–⟨CH₃⟩ | " | SO₂N(CH₃)₂ | " |
| 22 | (CH₃)₂NO₂S–⟨OCH₂COCH⟩ | –C₂H₄OCOO–⟨⟩ | CH₃ | CON(CH₃)₂ | yellow |
| 23 | HOOC–⟨HOOC⟩ | –C₂H₄OCON(CH₃)₂ | " | CN | " |
| 24 | ⟨COOH⟩–N=N–⟨CH₃⟩ | –CH₂COCH₃ | " | SO₂–N⟨piperidine H⟩ | orange |
| 25 | ⟨OCH₃, COOH⟩ | –C₂H₄CO–⟨⟩ | " | CN | reddish yellow |
| 26 | HOOC–⟨thiazole⟩ | –C₂H₄SO₂–⟨⟩ | " | " | orange |
| 27 | HOOC–H₂CO–⟨⟩–N=N–⟨OCH₃, CH₃⟩ | ⟨sulfolane ring: H₂C-CH(CH₃)-CH₂-CH₂-SO₂⟩ | " | " | red |

| | D | R₁ | R₂ | R₃ | Shade |
|---|---|---|---|---|---|
| 28 | 3-(SC₂H₄COOH)-phenyl-N=N-(2,5-dimethoxyphenyl)- | -C₂H₄NHCO-C₆H₅ | CH₃ | CN | red |
| 29 | 6-HOOC-benzothiazol-2-yl- | -C₂H₄-N(succinimido) | '' | '' | scarlett |
| 30 | 4-HOOC-C₆H₄-N=N-(3-Cl-phenyl)- | -CH₂-C₆H₅ | '' | COOC₂H₅ | orange |
| 31 | 4-O₂N-C₆H₄-N=N-(2-OCH₂COOH-phenyl)- | 3-CH₃-C₆H₄- | '' | CN | '' |
| 32 | HOOCH₂CO-C₆H₄- | 4-OCH₃-C₆H₄- | '' | '' | yellow |
| 33 | 4-HOOC-C₆H₄-(thiadiazol-2-yl)- | 3-Cl-C₆H₄- | '' | '' | reddish yellow |
| 34 | HOOC-C₆H₄- | -NH₂ | CH₃ | CN | yellow |
| 35 | 2-(SCH₂COOH)-phenyl- | -NH-C₆H₅ | -C₂H₄OCH₃ | '' | '' |
| 36 | 4-HOOC-C₆H₄-(thiadiazol-2-yl)- | -NHCH₃ | -C₆H₅ | '' | scarlet |
| 37 | HOOC-H₂C-C₆H₄- | N(CH₃)₂ | CH₃ | '' | yellow |
| 38 | HOOCHC=HC-C₆H₄- | NHCH₂-C₆H₅ | '' | '' | '' |
| 39 | HOOC-C₆H₄-N=N-(2-CH₃-phenyl)- | NHC₆H₁₃ | '' | '' | orange |
| 40 | 5-HOOC-phthalimido-N-C₆H₄- | -N(SO₂)(morpholine-like) | '' | '' | yellow |
| 41 | HOOC-H₆C₃S-C₆H₄- | -NH-(3-CH₃-C₆H₄) | -C₂H₅ | CN | yellow |
| 42 | 4-(OC₃H₆COOH)-phenyl- | -NH-(piperidinyl) | -CH₂CN | '' | '' |

| | D | R₁ | R₂ | R₃ | Shade |
|---|---|---|---|---|---|
| 43 | 4-NO₂, 2-CH₃, 1-(OC₂H₄COOH)-cyclohexyl | -NH-(2-thiazolyl) | -CH₃ | " | " |
| 44 | 3-COOH-phenyl | -NH-C(=N-)-N=C(OCH₃)-CH=C(OCH₃)- (dimethoxypyrimidinylamino) | " | " | " |
| 45 | 3-COOH-phenyl-N=N-[4-hydroxy-3-(1-tolyl-5-methylpyrazolyl)] | H | " | " | orange |
| 46 | 4-HOOC-phenyl-N=N-[4-hydroxy-3-(1-phenyl-5-methylpyrazolyl)] | H | -CH₃ | CN | orange |
| 47 | 4-HOOC-phenyl | " | " | " | yellow |
| 48 | 3-COOH-phenyl-N=N-(4-methylphenyl) | " | " | " | orange |
| 49 | 3-COOH-phenyl-N=N-(3,5-dimethylphenyl) | " | " | " | " |
| 50 | 3-COOH-phenyl-N=N-(3-methoxy-5-methylphenyl) | " | " | " | scarlet |
| 51 | 3-COOH-phenyl-N=N-(3,5-dimethoxyphenyl) | " | "" | red | |
| 52 | 4-HOOC-phenyl | H | -C₂H₄O-phenyl | -SO₂CH₃ | yellow |
| 53 | 3-COOH-phenyl | " | -CH₂-(piperidinyl) | -CN | " |
| 54 | " | | -CH₂-(thiazolyl) | " | " |
| 55 | " | | -CH₂-(furyl) | -SO₂-phenyl | " |

-continued

| | D | R₁ | R₂ | R₃ | Shade |
|---|---|---|---|---|---|
| 56 | " | " | —CH₂COOC₂H₅ | —CN | " |
| 57 | " | " | —CH₃ | —COOH₃ | " |
| 58 | " | " | —C₆H₅ (phenyl) | —CN | " |
| 59 | 4-OCH₃, 3-COOH phenyl | " | —CH₃ | " | " |
| 60 | 4-OSO₂N(CH₃)₂ phenyl | H | —CH₂COOH | —CN | yellow |
| 61 | Cl—C₆H₄— | —CH₃ | " | " | " |
| 62 | O₂N—C₆H₄— | —C₂H₄OH | " | " | " |
| 63 | 4-OCH₃, 3-SO₂N(C₂H₅)₂ phenyl | —C₄H₉ | " | " | " |
| 64 | 5-phenyl-1,3,4-thiadiazol-2-yl | H | " | —SO₂—C₆H₅ | scarlet |
| 65 | 4-OSO₂C₂H₅ phenyl | " | " | —SO₂N(morpholino) | yellow |
| 66 | 4-OSO₂C₆H₅ phenyl | —CH₂COOH | —CH₃ | —CN | " |
| 67 | 6-Cl-benzothiazol-2-yl | —C₂H₄COOH | —CH₃ | —SO₂CH₃ | scarlet |
| 68 | 5-phenyl-1,3,4-thiadiazol-2-yl | —NHCO—C₆H₄—COOH | " | —CN | " |
| 69 | 2,4,5-tri-CH₃ phenyl | —C₆H₅ | —CH₂COOH | " | yellow |
| 70 | 1,3,4-thiadiazol-2-yl | —C₆H₄—COOH | —CH₃ | " | scarlet |
| 71 | (CH₃)₂NCO—O—C₆H₄— | —CH₂—C₆H₄—COOH | " | " | yellow |
| 72 | H₅C₂OOC—C₆H₄— | H | —C₂H₄COOH | " | " |

-continued

| | D | R₁ | R₂ | R₃ | Shade |
|---|---|---|---|---|---|
| 73 | 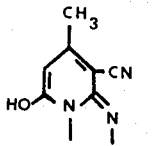 | —NHC₂H₄COOH | —CH₃ | " | orange |
| 74 |  | —NH—⌬—COOH | —CH₃ | —CN | scarlet |
| 75 | 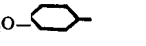 | —C₃H₆OCH(CH₃)₂ | —CH₂COOH | " | orange |
| 76 | ⌬—N=N—⌬ | " | " | " | " |
| 77 | HOH₄C₂O—⌬—N=N—⌬(OCH₃)(CH₃) | " | " | " | scarlet |
| 78 | HO—⌬—N=N—⌬ | —C₂H₅ | " | " | " |
| 79 | CH₃COHN—⌬—N=N—⌬(H) | " | " | " | " |
| 80 | HOOC—⌬ | H | —COOC₂H₅ | " | yellow |
| 81 | " | " | —CON(CH₃)₂ | " | " |
| 82 | HOOCCH₂O—⌬ | H | —CH₃ | —CN | " |

| | D | Coupling Component | Shade |
|---|---|---|---|
| 83 | ⌬—COOH |  | yellow |
| 84 | HOOCCH₂O—⌬ | " | " |
| 85 | HOOC—⌬—N=N—⌬ | " | orange |
| 86 | HOOC—⌬ | 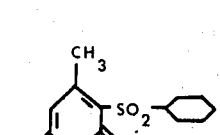 | yellow |

EXAMPLE 5

19.8 Parts of 3,3'-diaminodiphenylmethane are dissolved in 58 parts by volume of concentrated hydrochloric acid and 400 parts of water. The solution is diazotised at 0°–5°C by addition of 50 parts by volume of 4N sodium nitrite solution. The diazo solution is added to a solution of 44.4 parts of 3-cyano-6-hydroxy-4-carboxymethyl-1-ethyl-2-pyridone in 1000 parts of alcohol. The coupling mixture is rendered alkaline to Congo red with sodium acetate solution. Upon completion of the coupling the precipitated dyestuff is washed with water and dried. The dyestuff of the formula

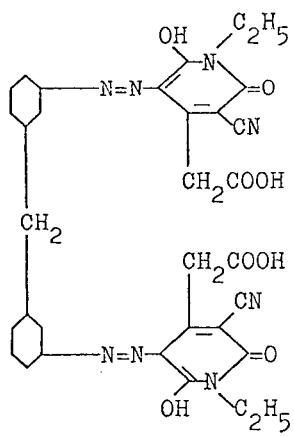

dyes polyester fibres in yellow shades having very good fastness properties.

EXAMPLE 6

4.55 Parts of sodium nitrite are sprinkled into 54 parts of concentrated sulphuric acid at 0° to 10°C. The mixture is heated to 65°C until everything is dissolved and the solution then cooled to 0°C. 60 Parts by volume of a mixture of glacial acetic acid and propionic acid in the ratio 4:1 are then added dropwise. A solution of 4.56 parts of 3,5-diaminobenzoic acid in 60 parts by volume of a mixture of glacial acetic acid and propionic acid (4:1) are added dropwise to the resulting solution and the reaction mixture is stirred for 2 hours at 0° to 5°C. To this diazo solution are added 4.55 parts of urea by small amounts. The resulting diazo solution is added at 0° to 5°C to a solution of 9.45 parts of 3-cyano-6-hydroxy-4-methyl-2-pyridone in 200 parts of alcohol. The mixture is further stirred for 15 minutes and then rendered alkaline to Congo red with sodium acetate solution. The precipitated dyestuff is filtered off, washed with water until free from salt and dried. The dyestuff of the formula

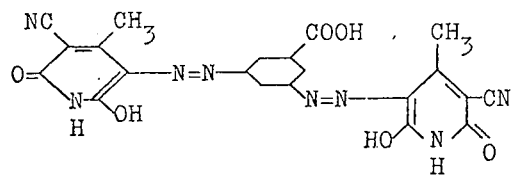

dyes polyester fibres in yellow shades having very good fastness properties.

A dyestuff possessing similar properties is obtained if m-phenyldiamine is diazotised according to the same process and coupled with 3-cyano-6-hydroxy-4-carboxymethyl-2-pyridone.

EXAMPLE 7

133 Parts of a 10% paste of the dyestuff obtained according to Example 1, 200 parts of 2.5% sodium alginate solution, 1.5 parts by volume of 40% of acetic acid are made up to 1000 parts with water. Polyester fabric is padded with this dyebath and squeezed out to a 75% retention of liquid. The fabric is dried for 1 minute at 120°C and a portion of the dried fabric is printed with a white resist as follows: a paste consisting of 20 parts of soda and 950 parts of 2.5% sodium alginate solution is printed in stripes on the fabric. The fabric is thermofixed in this state for 1 minute at 200°C and subsequently thoroughly washed with a solution which contains the adduct of 9 moles of ethylene oxide with 1 mol of nonylphenyl. A yellow dyed fabric is obtained wiith a white resist.

The printing paste can furthermore be prepared with additives such as alumium sec.-butylate or m-nitrobenzenesulphonate.

EXAMPLE 8

1 Part of the dyestuff obtained according to Example 3 is ground wet with 2 parts of a 50% aqueous solution of the sodium salt of dinaphthylmethanedisulphonic acid.

This dyestuff preparation is stirred with 40 parts of a 10% aqueous solution of the sodium salt of N-benzyl-$\mu$-heptadecyl-benzimidazole-disulphonic acid and 4 parts of a 40% acetic acid solution are added. A dyebath of 4000 parts is prepared therefrom by dilution with water.

100 Parts of a purified polyester fabric are introduced into this bath at 50°C, the temperature is raised within half an hour to 120°–130°C and dyeing is carried out for 1 hour in a sealed vessel at this temperature. The fabric is subsequently thoroughly rinsed. A powerful, pure, orange dyeing is obtained.

1. A process for coloring synthetic polyester textile materials which comprises applying to said materials, by a dyeing, padding or printing process, an aqueous dispersion of an azo compound of the formula

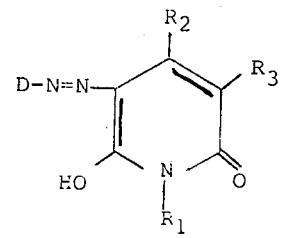

wherein
D represents the radical of a diazo component,
$R_1$ and $R_3$ each represent a hydrogen atom or a substituent and
$R_2$ represents a substituent, said compound containing at least one carboxy group, that may not, however, be bonded in the adjacent position to the azo bridge directly to the ring.

2. A process for coloring synthetic polyester textile materials which comprises applying to said materials, by a dyeing, padding or printing process, an aqueous dispersion of an azo compound of the formula

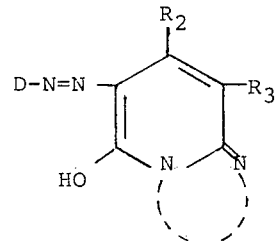

wherein the two nitrogen atoms of the pyridone radical are bonded to one another via a carbon bridge to form a second ring,
D represents the radical of a diazo component,
$R_3$ represents a hydrogen atom or a substituent and
$R_2$ represents a substituent, said compound containing at least one carboxy group that may not, however, be bonded in the adjacent position to the azo bridge directly to the ring.

3. A process according to claim 1, wherein the process is a printing process.

4. A process according to claim 3, wherein the printing process is a resist printing process.

5. The colored synthetic polyester textile materials produced by the process of claim 1.

6. The colored synthetic polyester textile material produced by the process of claim 2.

* * * * *